United States Patent

Wünsch et al.

[11] Patent Number: 5,847,055
[45] Date of Patent: Dec. 8, 1998

[54] POLYMER-CONTAINING CATALYST SYSTEMS

[75] Inventors: Josef Wünsch, Schifferstadt; Walter Maier, Mannheim, both of Germany

[73] Assignee: BASF Aktiengesellschaft, Ludwigshafen, Germany

[21] Appl. No.: 894,482

[22] PCT Filed: Feb. 13, 1996

[86] PCT No.: PCT/EP96/00597

§ 371 Date: Aug. 22, 1997

§ 102(e) Date: Aug. 22, 1997

[87] PCT Pub. No.: WO96/26226

PCT Pub. Date: Aug. 29, 1996

[30] Foreign Application Priority Data

Feb. 24, 1995 [DE] Germany ............... 19506553

[51] Int. Cl.[6] ........................ C08F 8/42
[52] U.S. Cl. .......... 525/370; 525/33.03; 525/332.3; 525/333.3; 525/360; 526/170; 526/171; 526/183; 526/190; 526/943; 502/109; 502/152
[58] Field of Search ................. 526/170, 160, 526/904, 943, 171, 183, 190; 502/109, 152, 108; 525/370, 360, 333.3, 332.3, 330.3

[56] References Cited

U.S. PATENT DOCUMENTS

| | | | |
|---|---|---|---|
| 3,396,155 | 8/1968 | Delbouille et al. | 526/904 X |
| 3,933,770 | 1/1976 | Ikeda et al. | |
| 4,290,918 | 9/1981 | Bayer et al. | |
| 4,426,318 | 1/1984 | Fries et al. | 526/904 X |
| 4,725,568 | 2/1988 | Parker et al. | 525/370 X |
| 5,492,978 | 2/1996 | Peifer et al. | 525/370 X |

FOREIGN PATENT DOCUMENTS

| | | |
|---|---|---|
| 8 409 | 3/1980 | European Pat. Off. |
| 206 794 | 12/1986 | European Pat. Off. |
| 416 815 | 3/1991 | European Pat. Off. |
| 535 582 | 4/1996 | European Pat. Off. |
| 24 12 105 | 4/1975 | Germany |
| 43 03 647 | 8/1994 | Germany |

OTHER PUBLICATIONS

Anionic polymerization:, Morton, Academic PRess (1983).
Breslow et al., J.A.M. Chem. Soc., (1959) 81 S. 81–86
Beilstein 5, 1922, S. 367/474/485.

*Primary Examiner*—Fred Teskin
*Attorney, Agent, or Firm*—Keil & Weinkauf

[57] ABSTRACT

A catalyst system of the formula I X M $(Z^1)_{z_1}(Z^2)_{z_2}(Z^3)_{z_3}$ I where X is $C_1$–$C_{10}$-alkyl, 5- to 7-membered cycloalkyl, $C_1$–$C_{10}$-alkoxy, $C_6$–$C_{15}$-aryl or a compound of the formula II

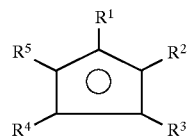

where $R^1$ to $R^5$ are substituents as defined in the specification, M is a metal of transition groups II to VIII of the Periodic Table of the Elements, $Z^1$ to $Z^3$ are polymers of vinylaromatic compounds, dienes, acrylates or their mixtures and $z_1$ to $z_3$ are 0, 1, 2 or 3, where $\leq z_1 + z_2 + z_3 \leq 3$.

7 Claims, No Drawings

POLYMER-CONTAINING CATALYST SYSTEMS

The present invention relates to catalyst systems of the formula I

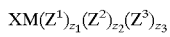

where the substituents and indices have the following meanings:

X is $C_1$–$C_{10}$-alkyl, 5- to 7-membered cycloalkyl, $C_1$–$C_{10}$-alkoxy, $C_6$–$C_{15}$-aryl or a compound of the formula II

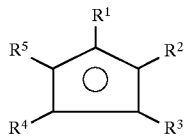

where $R^1$ to $R^5$
are hydrogen, $C_1$–$C_{10}$-alkyl which may bear from 1 to 5 halogen substituents, 5- to 7-membered cycloalkyl which may in turn bear $C_1$–$C_6$-alkyl groups as substituents, $C_6$–$C_{15}$-aryl or arylalkyl, where two adjacent radicals may also together form a cyclic group having from 4 to 15 carbon atoms, or halogen, $C_1$–$C_{10}$-alkoxy, $NR^6R^7$ or $Si(R^6)_3$,
and $R^6$ and $R^7$
are hydrogen, $C_1$–$C_{10}$-alkyl, $C_6$–$C_{15}$-aryl or $C_3$–$C_{10}$-cycloalkyl,
M is a metal of transition groups II to VIII of the Periodic Table of the Elements,
$Z^1$ to $Z^3$
are polymers of vinylaromatic compounds, dienes, acrylates or their mixtures
and $Z_1$ to $Z_3$
are 0, 1, 2 or 3, where $1 \leq z_1+z_2+z_3 \leq 3$.

The present invention further relates to a process for preparing such catalyst systems and also their use for preparing polymers of vinylaromatic compounds.

Catalyst systems containing transition metals as active catalyst center are widely used in industry for preparing polymers.

Thus, D. S. Breslow, N. R. Newburg, J. Am. Chem. Soc. 81 (1959), pp. 81–86 discloses homogeneous Ziegler-Natta catalysts.

EP-A 416 815 describes metallocenes in which two aromatic ligands are bridged via carbon or silyl groups.

Furthermore, DE-A 43 03 647 discloses donor-containing catalyst systems.

These known catalyst systems can also be in supported form. Disadvantages of the known systems are that the mass transfer to and through the support is limited, that the selectivity is too low for some applications and that only a relatively small proportion of the metal centers present is catalytically active.

It is an object of the present invention to provide new catalyst systems which do not have the disadvantages mentioned, which can, in particular, be readily separated from the polymer formed and which can be easily activated.

We have found that this object is achieved by the catalyst systems defined in the introduction.

The present invention also provides a process for preparing such catalyst systems and provides for their use for preparing polymers of vinylaromatic compounds.

Among the novel catalyst systems of the formula I

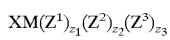

preference is given to those in which X is $C_1$–$C_4$-alkyl, in particular methyl or ethyl, $C_1$–$C_4$-alkoxy or particularly preferably a compound of the formula II

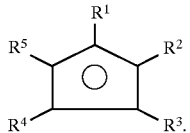

Among the compounds of the formula II, preference is given to those in which $R^1$ to $R^5$ are hydrogen, $C_1$–$C_4$-alkyl, in particular methyl, $C_6$–$C_{15}$-aryl, in particular phenyl and biphenyl, or where two adjacent radicals together form a cyclic group having from 4 to 15 carbon atoms, in which case X is, for example, indenyl, benzindenyl or fluorenyl, each of which may in turn be substituted by alkyl radicals.

X is particularly preferably pentamethylcyclopentadienyl.

If X is a compound of the formula II, the catalyst systems of the present invention are semisandwich complexes.

The metal M is preferably an element of transition groups IV to VI of the Periodic Table, in particular an element of transition group IV, viz. titanium, zirconium or hafnium, preferably titanium.

$Z^1$ to $Z^3$ are polymers of vinylaromatic compounds, dienes such as butadiene or isoprene, acrylates preferably having from 1 to 6 carbon atoms in the ester radical, in particular butyl acrylate, or their mixtures so that $Z^1$ to $Z^3$ are then copolymers.

$Z^1$ to $Z^3$ are preferably polymers of vinylaromatic compounds of the formula III

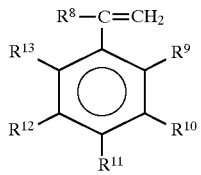

where the substituents have the following meanings:
$R^8$ is hydrogen or $C_1$–$C_4$-alkyl,
$R^9$ to $R^{13}$ are, independently of one another, hydrogen, $C_1$–$C_{12}$-alkyl, $C_6$–$C_{18}$-aryl, halogen or two adjacent radicals together form a cyclic group having from 4 to 15 carbon atoms.

Preference is given to vinylaromatic compounds of the formula III, in which
$R^8$ is hydrogen
and
$R^9$ to $R^{13}$ are hydrogen, $C_1$–$C_4$-alkyl, chlorine or phenyl or two adjacent radicals together form a cyclic group having from 4 to 15 carbon atoms, giving, for example, naphthalene derivatives or anthracene derivatives as compounds of the formula III.

Examples of such preferred compounds are:
Styrene, p-methylstyrene, p-chlorostyrene, 2,4-dimethylstyrene, 4-vinylbiphenyl, 2-vinylnaphthalene or 9-vinylanthracene.

Particularly preferred vinylaromatic compounds are styrene and p-methylstyrene.

The preparation of vinylaromatic compounds of the formula III is known per se and described, for example, in Beilstein 5, 367, 474, 485.

$Z^1$ to $Z^3$ are preferably polymers derived from the same compounds, particularly preferably polystyrenes. The molecular weights $M_n$ (number average) of $Z^1$ to $Z^3$ are in each case generally in the range from 500 to $10^8$ g/mol, preferably in the range from $10^3$ to $10^6$ g/mol.

A particularly preferred catalyst system of the present invention is that in which X is pentamethylcyclopentadienyl, M is titanium and $Z^1$ to $Z^3$ are polystyrenes.

The number $z_1$, $z_2$, $z_3$ of the respective polymers $Z^1$, $Z^2$, $Z^3$ depends essentially on the metal M. In the preferred case where M is a metal of transition group IV of the Periodic Table of the Elements, the sum $z_1+z_2+z_3$ is preferably 3.

In the catalyst systems of the present invention, the polymers $Z^1$ to $Z^3$ are covalently bonded to the metal M.

The novel catalyst systems of the formula I can be prepared by anionically polymerizing the vinylaromatic compounds, dienes, acrylates or mixtures thereof which lead to the polymers $Z^1$ to $Z^3$ and then reacting the reaction mixture with a transition metal salt of the formula IV $$XMY_y \qquad \qquad IV$$

where Y is fluorine, chlorine, bromine or iodine and y is 1, 2 or 3.

The anionic polymerization of vinylaromatic compounds, dienes, acrylates or their mixtures is known per se and described in Maurice Morton, Anionic Polymerization: Principles and Practice, Academic Press, 1983. The anionic polymerization is customarily carried out by addition of alkali metal compounds, for example phenyllithium, sodium methoxide, n-butyllithium or sec-butyllithium to the monomer. A transition metal salt of the formula IV is then added to this still living, anionic polymer. Among these salts, preference is given to those in which Y is chlorine or bromine, in particular chlorine.

As regards the preferred compounds which lead to the polymers $Z^1$ to $Z^3$ as well as the substituents X and the metal M in the formula IV, what has been said for the catalyst systems of the formula I applies.

The reaction conditions are not critical per se. The reaction temperature is generally in the range from $-75°$ to $150°$ C., preferably from $-10°$ to $100°$ C.

The molar amount of transition metal salt is preferably from 0.001 to 2.0 molar equivalents, based on the amount of alkali metal compound in the anionic polymerization.

It has been found to be useful for the transition metal salt of the formula IV to be dissolved in an inert solvent. Suitable solvents are hydrocarbons such as pentane or hexane, benzene, toluene, xylenes, ethers such as diethyl ether or tetrahydrofuran or mixtures thereof.

The catalyst systems of the present invention are suitable for preparing polymers of vinylaromatic compounds and can be readily separated from the polymer formed, can be easily activated and are simple to prepare industrially.

EXAMPLE

Preparation of pentamethylcyclopentadienyltris(polystyryl)titanium

Under an inert gas atmosphere in a 500 ml flask, 31.25 g (0.3 mol) of unstabilized styrene were dissolved in 200 ml of n-hexane and heated to 60° C.

60 mmol of sec-butyllithium were then added at 60° C. to this mixture and polymerization was carried out for 1 hour under an insert gas atmosphere.

This mixture was subsequently added to 5.0 g (18.22 mmol) of pentamethylcyclopentadienyltitanium trichloride in 125 ml of n-hexane and cooled to 0° C. It was then stirred for 12 hours at room temperature. The product formed was filtered off under an inert gas atmosphere and recrystallized from n-hexane. The filtered residue was dried at 40° C. for 4 hours under reduced pressure.

Yield: 23.5 g (68%)

Color: violet-blue
$^{13}$C-NMR:($d_8$-THF) $\delta$=14.5 ppm [$CH_3$];
$\delta$=25.7 ppm; 27.7; 32.5 [$CH_2$];
$\delta$=41.4 ppm; 41.5 [CH];
$\delta$=64.7 ppm [Ti-CH];
$\delta$=126.2; 126.5; 128.5; 128.8 [aryl-CH];
$\delta$=132.3; 134.7; 137.9 [Cp-C];
$\delta$=146.2; 146.7 [aryl-C]

The NMR signal at $\delta$=64.7 ppm is evidence of the covalent titanium-methyne unit of the polystyryl chains.

We claim:

1. A catalyst system of the formula I $$XM(Z^1)_{z_1}(Z^2)_{z_2}(Z^3)_{z_3} \qquad \qquad I$$

where the substituents and indices have the following meanings:

X is $C_1-C_{10}$-alkyl, 5- to 7-membered cycloalkyl, $C_1-C_{10}$-alkoxy, $C_6-C_{15}$-aryl or a compound of the formula II

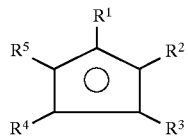

II where $R^1$ to $R^5$ are hydrogen, $C_1-C_{10}$-alkyl which may bear from 1 to 5 halogen substituents, 5- to 7-membered cycloalkyl which may in turn bear $C_1-C_6$-alkyl groups as substituents, $C_6-C_{15}$-aryl or arylalkyl, where two adjacent radicals may also together form a cyclic group having from 4 to 15 carbon atoms, or halogen, $C_1-C_{10}$-alkoxy, $NR^6R^7$ or $Si(R^6)_3$, and $R^6$ and $R^7$ are hydrogen, $C_1-C_{10}$-alkyl, $C_6-C_{15}$-aryl or $C_3-C_{10}$-cycloalkyl, M is a metal of transition groups II to VIII of the Periodic Table of the Elements, $Z^1$ to $Z^3$ are polymers of vinylaromatic compounds, dienes, acrylates or their mixtures and $z_1$ to $z_3$ are 0, 1, 2 or 3, where $1 \leq z_1+z_2+z_3 \leq 3$.

2. The catalyst system of claim 1, wherein X is a compound of the formula II.

3. The catalyst system of claim 1, wherein M is a metal of transition groups IV to VI of the Periodic Table of the Elements.

4. The catalyst system of claim 1, wherein $Z^1$ to $Z^3$ are polymers of vinylaromatic compounds of the formula III

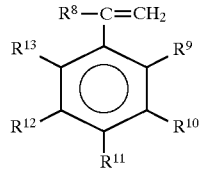

III where the substituents have the following meanings:

$R^8$ is hydrogen or $C_1-C_4$-alkyl, $R^9$ to $R^{13}$ are, independently of one another, hydrogen, $C_1-C_{12}$-alkyl, $C_6-C_{18}$-aryl, halogen or two adjacent radicals together form a group having from 4 to 15 carbon atoms.

5. A process for preparing a catalyst system as defined in claim 1, which comprises anionically polymerizing the vinylaromatic compounds, dienes, acrylates or mixtures thereof which lead to the polymers $Z^1$ to $Z^3$ and then reacting the reaction mixture with a transition metal salt of the formula IV $$XMY_y \quad\quad IV$$

where Y is fluorine, chlorine, bromine or iodine and y is 1, 2 or 3.

6. The process of claim 5, wherein the transition metal salt IV is dissolved in an inert solvent.

7. The catalyst system of claim 2, wherein M is a metal of transition groups IV to VI of the Periodic Table of the Elements.

* * * * *